(12) United States Patent
Brandwein et al.

(10) Patent No.: US 10,035,008 B2
(45) Date of Patent: Jul. 31, 2018

(54) SYSTEM AND METHOD FOR TOOL FEEDBACK SENSING

(75) Inventors: David H. Brandwein, New Brighton, MN (US); Franklyn L. Frederickson, White Bear Lake, MN (US); Karl M. Kropp, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1709 days.

(21) Appl. No.: 11/910,173

(22) PCT Filed: Apr. 7, 2006

(86) PCT No.: PCT/US2006/013608
§ 371 (c)(1),
(2), (4) Date: Sep. 28, 2007

(87) PCT Pub. No.: WO2006/108185
PCT Pub. Date: Oct. 12, 2006

(65) Prior Publication Data
US 2008/0208146 A1    Aug. 28, 2008

Related U.S. Application Data

(60) Provisional application No. 60/669,133, filed on Apr. 7, 2005.

(51) Int. Cl.
*A61M 37/00* (2006.01)
*A61B 5/145* (2006.01)

(52) U.S. Cl.
CPC ..... *A61M 37/0015* (2013.01); *A61B 5/14514* (2013.01); *A61M 2037/0023* (2013.01)

(58) Field of Classification Search
CPC ...... A61B 5/14514; A61M 2037/0023; A61M 37/0015
USPC ..... 604/173, 264, 272, 46, 48, 500, 506, 73, 604/80, 93.01; 606/186
See application file for complete search history.

(56) References Cited

U.S. PATENT DOCUMENTS

| | | |
|---|---|---|
| 3,034,507 A | 5/1962 | McConnell et al. |
| 3,072,122 A | 1/1963 | Rosenthal |
| 3,123,212 A | 3/1964 | Taylor et al. |
| 3,136,314 A | 6/1964 | Kravitz |
| RE25,637 E | 9/1964 | Kravitz et al. |
| 3,221,740 A | 12/1965 | Rosenthal |

(Continued)

FOREIGN PATENT DOCUMENTS

| | | |
|---|---|---|
| EP | 407063 | 1/1991 |
| GB | 1080986 | 8/1967 |

(Continued)

OTHER PUBLICATIONS

Daddona, Current Opinion in Drug Discovery and Development 1999 2(2);168-171.

(Continued)

*Primary Examiner* — Imani Hayman

(57) ABSTRACT

A microneedle application device for moving a microneedle array toward a target skin location includes a feedback sensor. The feedback sensor is operably connected to the microneedle application device, and is capable of generating an output corresponding to forces between the target skin location and the microneedle application device.

17 Claims, 9 Drawing Sheets

(56) References Cited

U.S. PATENT DOCUMENTS

| | | | |
|---|---|---|---|
| 3,246,647 A | 4/1966 | Taylor et al. | |
| 3,322,121 A | 5/1967 | Banker | |
| 3,466,131 A | 9/1969 | Arcudi | |
| 3,510,933 A | 5/1970 | Taylor et al. | |
| 3,512,520 A | 5/1970 | Cowan | |
| 3,596,660 A | 8/1971 | Melone | |
| 3,675,766 A | 7/1972 | Rosenthal | |
| 3,678,150 A | 7/1972 | Szumski et al. | |
| 3,688,764 A | 9/1972 | Reed et al. | |
| 3,905,371 A | 9/1975 | Stickl et al. | |
| 3,964,482 A | 6/1976 | Gerstel et al. | |
| 4,109,655 A | 8/1978 | Chacornac | |
| 4,237,906 A | 12/1980 | Havstad et al. | |
| 4,304,241 A | 12/1981 | Brennan | |
| 4,360,016 A | 11/1982 | Sarrine | |
| 4,453,926 A | 6/1984 | Galy | |
| 4,503,856 A | 3/1985 | Cornell et al. | |
| 4,517,978 A | 5/1985 | Levin et al. | |
| 4,637,403 A | 1/1987 | Garcia et al. | |
| 4,858,607 A | 8/1989 | Jordan et al. | |
| 4,869,249 A | 9/1989 | Crossman et al. | |
| 4,920,977 A | 5/1990 | Haynes | |
| 4,924,879 A | 5/1990 | O'Brien | |
| 5,209,967 A | 5/1993 | Wright et al. | |
| 5,250,023 A | 10/1993 | Lee et al. | |
| 5,318,584 A | 6/1994 | Lange et al. | |
| 5,368,047 A | 11/1994 | Suzuki et al. | |
| 5,402,798 A | 4/1995 | Swierczek et al. | |
| 5,487,726 A | 1/1996 | Rabenau et al. | |
| 5,573,626 A | 11/1996 | Rossini et al. | |
| 5,611,806 A | 3/1997 | Jang | |
| 5,879,326 A | 3/1999 | Godshall et al. | |
| 5,904,978 A | 5/1999 | Hanrahan et al. | |
| 5,983,136 A | 11/1999 | Kamen | |
| 6,050,988 A | 4/2000 | Zuck | |
| 6,132,755 A | 10/2000 | Eicher et al. | |
| 6,256,533 B1 | 7/2001 | Yuzhakov et al. | |
| 6,293,925 B1 | 9/2001 | Safabash et al. | |
| 6,312,612 B1 | 11/2001 | Sherman et al. | |
| 6,322,808 B1 | 11/2001 | Trautman et al. | |
| 6,334,856 B1 | 1/2002 | Allen et al. | |
| 6,440,096 B1 | 8/2002 | Lastovich et al. | |
| 6,454,755 B1 | 9/2002 | Godshall | |
| 6,503,231 B1 | 1/2003 | Prausnitz et al. | |
| 6,532,386 B2 * | 3/2003 | Sun et al. | 604/20 |
| 6,537,242 B1 | 3/2003 | Palmer | |
| 6,547,755 B1 * | 4/2003 | Lippe et al. | 604/67 |
| 6,589,202 B1 | 7/2003 | Powell | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,623,457 B1 | 9/2003 | Rosenberg | |
| 6,656,147 B1 * | 12/2003 | Gertsek et al. | 604/28 |
| 6,713,291 B2 | 3/2004 | King et al. | |
| 6,743,211 B1 | 6/2004 | Prausnitz et al. | |
| 6,797,276 B1 | 9/2004 | Glenn et al. | |
| 6,855,131 B2 | 2/2005 | Trautman et al. | |
| 6,881,203 B2 | 4/2005 | Delmore et al. | |
| 6,890,319 B1 | 5/2005 | Crocker | |
| 6,908,453 B2 | 6/2005 | Fleming et al. | |
| 6,931,277 B1 | 8/2005 | Yuzhakov et al. | |
| 2002/0032415 A1 | 3/2002 | Trautman et al. | |
| 2002/0058902 A1 * | 5/2002 | Kollias et al. | 604/20 |
| 2002/0082543 A1 | 6/2002 | Park et al. | |
| 2002/0087182 A1 | 7/2002 | Trautman et al. | |
| 2002/0091357 A1 | 7/2002 | Trautman et al. | |
| 2002/0095134 A1 | 7/2002 | Pettis et al. | |
| 2002/0111600 A1 | 8/2002 | Cormier et al. | |
| 2002/0123675 A1 | 9/2002 | Trautman et al. | |
| 2002/0138049 A1 | 9/2002 | Allen et al. | |
| 2002/0169416 A1 | 11/2002 | Gonnelli et al. | |
| 2002/0177858 A1 | 11/2002 | Sherman et al. | |
| 2002/0188245 A1 | 12/2002 | Martin et al. | |
| 2002/0198509 A1 | 12/2002 | Mikszta et al. | |
| 2003/0050602 A1 | 3/2003 | Pettis et al. | |
| 2003/0083641 A1 * | 5/2003 | Angel et al. | 604/500 |
| 2003/0135158 A1 | 7/2003 | Gonnelli | |
| 2003/0181863 A1 | 9/2003 | Ackley et al. | |
| 2003/0199812 A1 | 10/2003 | Rosenberg | |
| 2003/0199823 A1 | 10/2003 | Bobroff et al. | |
| 2003/0208167 A1 | 11/2003 | Prausnitz et al. | |
| 2004/0049150 A1 | 3/2004 | Dalton et al. | |
| 2004/0077994 A1 | 4/2004 | Lastovich et al. | |
| 2004/0138612 A1 | 7/2004 | Shermer et al. | |
| 2004/0176732 A1 | 9/2004 | Frazier et al. | |
| 2004/0181203 A1 | 9/2004 | Cormier et al. | |
| 2005/0025778 A1 | 2/2005 | Cormier et al. | |
| 2005/0027242 A1 | 2/2005 | Gabel et al. | |
| 2005/0065463 A1 | 3/2005 | Tobinaga et al. | |
| 2005/0065466 A1 | 3/2005 | Vedrine | |
| 2005/0065472 A1 | 3/2005 | Cindrich et al. | |
| 2005/0096586 A1 | 5/2005 | Trautman et al. | |
| 2005/0106226 A1 | 5/2005 | Cormier et al. | |
| 2005/0137525 A1 | 6/2005 | Wang et al. | |
| 2005/0261631 A1 | 11/2005 | Clarke et al. | |

FOREIGN PATENT DOCUMENTS

| | | |
|---|---|---|
| GB | 2064329 | 6/1981 |
| GB | 2221394 | 2/1990 |
| WO | WO 96/10630 | 4/1996 |
| WO | WO 00/56213 | 9/2000 |
| WO | WO 01/36037 | 5/2001 |
| WO | WO 2004/020034 | 3/2004 |
| WO | WO 2004/021882 | 3/2004 |
| WO | WO 05/51455 | 6/2005 |
| WO | WO 05/51476 | 6/2005 |
| WO | WO 05/65765 | 7/2005 |
| WO | WO 2005/123173 | 12/2005 |
| WO | WO 2006/055795 | 5/2006 |
| WO | WO 2006/055802 | 5/2006 |
| WO | WO 2006/108185 | 10/2006 |
| WO | WO 2007/002521 | 1/2007 |

OTHER PUBLICATIONS

Henry et al. J. Pharm.Sci., 1998, 87,8,922-925.

Kaushik et al. Anesthesia Analg., 2001, 92, 502-504.

McAllister et al. Annual Review of Biomedical Engineering, 2000, 2, 289-313.

McAllister et al. Proceed. Int'l. Symp. Control Release of Bioactive Material, 26, (1999), CRS, 192-193.

* cited by examiner

SYSTEM AND METHOD FOR TOOL FEEDBACK SENSING

CROSS-REFERENCE TO RELATED APPLICATIONS

The present application claims priority to U.S. Provisional Application Ser. No. 60/669,133, filed on Apr. 7, 2005, which is incorporated herein in its entirety.

BACKGROUND

The present invention relates to a system and method for tool feedback sensing. More particularly, the present invention relates to feedback sensing provided with tools for assisting with microneedle application procedures.

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle arrays can be used in conjunction with an applicator device capable of being used a number of different times. The applicator device can include a removable collar for holding the microneedle array prior to deployment. The collar can be reusable or disposable. The microneedle arrays are generally used once and then discarded. The arrays are typically manufactured in a flat sheet-like configuration and temporarily attached to the applicator device using, for example, an adhesive.

Devices exist in the market for making measurement of skin properties, such as Cutometers (skin elasticity), Reviscometers (skin construction), and contact Tonometers (time to rebound from a given deflection), but the suitability of these measurements for use in effectively characterizing microneedle application sites is not known.

SUMMARY

Research involving microneedle application may be conducted at application sites on different skin surfaces. For instance, tests may be performed involving microneedle arrays applied to particular skin target areas (e.g., forearms, buttocks, biceps, etc.) of a selected sample of like persons or to persons differing in some way (e.g., by age, race, gender, etc.) or to the skin of different species of test subjects.

The process of consistent use of microneedle application technology presents numerous challenges. Operation of microneedle applicator devices by operators, such as healthcare providers, can be problematic. Operator error, for example, can result in improper microneedle array deployment, which can undermine desired molecule transport. It is believed that proper applicator device positioning can affect microneedle array deployment. However, it is difficult to help ensure proper applicator device positioning. Additional problems are faced in research contexts. Variations across different application sites present difficulties in gathering reliable data from research tests, and in reliably applying collected research data to other contexts.

In one aspect, the present invention relates to a microneedle application device for moving a microneedle array toward a target skin location includes a feedback sensor. The feedback sensor is operably connected to the microneedle application device, and is capable of generating an output corresponding to forces between the target skin location and the microneedle application device.

In another aspect, the present invention relates to a method of microneedle application. The method comprises providing a microneedle applicator device, providing a microneedle array that is initially mounted to the microneedle applicator device, positioning a locating portion of the microneedle applicator device in contact with skin to substantially define a target application site on the skin for application of the microneedle array, sensing a force between the target application site and a first portion of the microneedle applicator device, positioning the microneedle applicator device such that the microneedle array can be moved into contact with the skin along a path that is substantially orthogonal relative to the target application site, and moving the microneedle array toward the target application site.

In another aspect, the present invention relates to a method of positioning a tool for assisting with microneedle application procedures. The method comprises placing the tool in contact with a target site, and sensing a pushback force of the target site against the tool.

In another aspect, the present invention relates to an applicator system including a microneedle application device and a force sensing element. The microneedle application device has a portion adapted for skin contact at least prior to microneedle application. The force sensing element is capable of sensing force between the portion of the microneedle applicator adapted for skin contact and a target application site.

In another aspect, the present invention relates to a tool for sensing forces between the tool and a skin surface. The tool includes a housing having a force application portion, a contact portion, a support, and a sensor. The contact portion is supported by the housing, and is capable of contacting the skin surface to substantially define a target location. The support is supported by the housing, and is capable of reaching the target location. The sensor is disposed between the target location and a first portion of the tool, and is capable of sensing force.

The above summary is not intended to describe each disclosed embodiment or every implementation of the present invention. The figures and the detailed description, which follow, more particularly exemplify illustrative embodiments.

Figure 1:
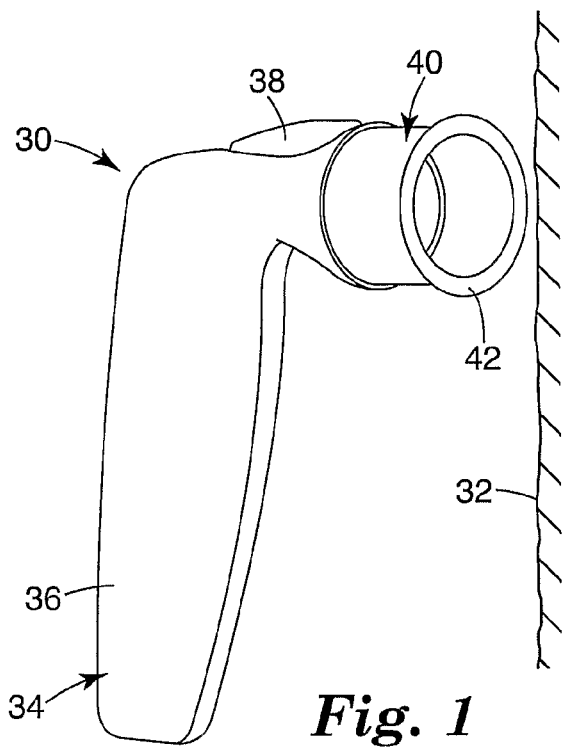
FIG. 1 is a perspective view of a microneedle application device and a target skin surface.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

The present invention relates to providing feedback for tools such as microneedle array application devices, as well as diagnostic instruments used in microneedle array application research and training (which may be configured to mimic or simulate typical microneedle application devices). One or more sensors are provided on the tool for sensing forces between the tool and a surface (such as a target skin surface) against which the tool is positioned. An output of the sensed forces can be provided. In some embodiments with multiple sensors, feedback provided according to the present invention permits an indication of how desirably orientated the tool is relative to the surface against which it is positioned. In addition, the present invention can be used for determining ideal locations on the body for application of microneedles.

Aspects of the present invention can be used in conjunction with a variety of tools, though particular advantages are provided for patch application devices. Patches can be used for transdermal delivery of molecules, and can carry microneedle arrays, which have utility for the delivery of large molecules that are ordinarily difficult to deliver by passive transdermal delivery. As used herein, "array" refers to the medical devices described herein that include one or more structures capable of piercing the stratum corneum to facilitate the transdermal delivery of therapeutic agents or the sampling of fluids through or to the skin. "Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

When the patch application devices are to be used for piercing the stratum corneum in preparation for transdermal drug delivery, the height of the microneedles is preferably sufficient to pass through the stratum corneum. It is also, however, preferable that the height of the microneedles is not sufficiently large to cause significant pain when inserted at a delivery site. In some instances, microneedles of the present invention may have a height of about 250 micrometers or less. In some instances, microneedles of the present invention may have a height of about 100 micrometers or more.

FIG. 1 is a perspective view of a microneedle application device 30 and a skin surface 32. The microneedle application device 30 can be used to deploy patches that include a microneedle array to a surface, such as to the skin surface 32. The device 30 has a housing 34 with a gripping portion 36, a trigger 38, and a collar 40. One embodiment of a microneedle application device 30 is disclosed in U.S. Provisional Patent Application Ser. No. 60/578,651, which is hereby incorporated by reference in its entirety.

The collar 40 defines an outward-facing contact portion 42. In one embodiment, the collar 40 is detachable from the housing 34, and can be disposable or reusable. As shown in FIG. 1, the collar 40 is a unitary member of generally cylindrical shape, and contact portion 42 is generally annular in shape. In further embodiments, the collar 40 can have nearly any shape and configuration. For example, the collar 40 can have a rectangular, triangular, oval, or other shape or combination of shapes. The contact portion 42 will typically have a shape corresponding to the shape of the collar 40. In addition, the collar 40 need not be unitary, and can be configured to form a number of discrete feet or supports that collectively define the contact portion 42.

Figure 2:
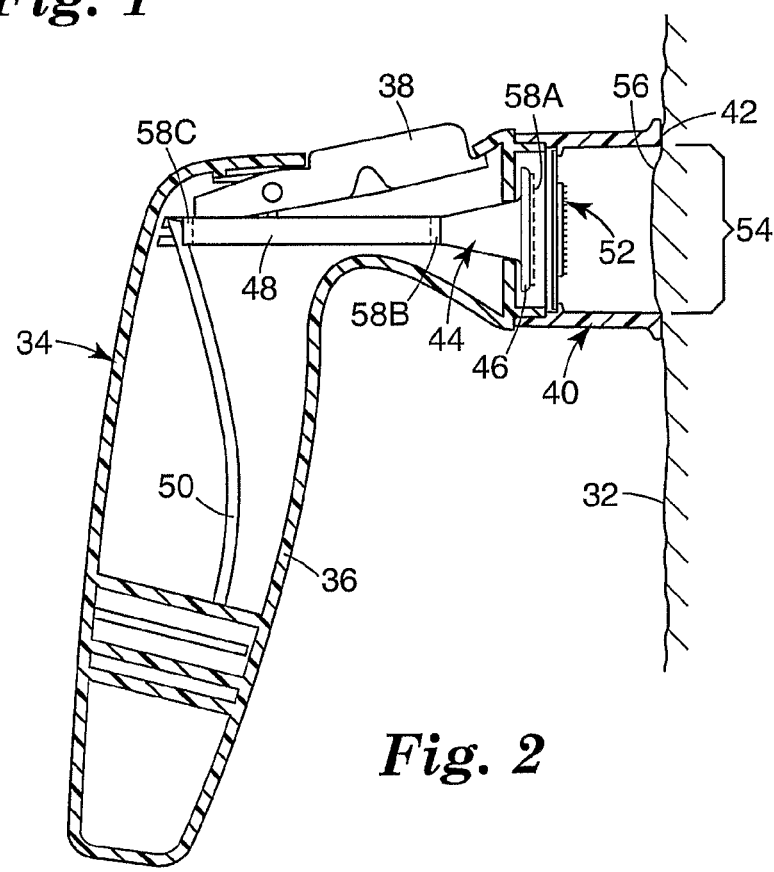
FIG. 2 is a cross sectional side view of the microneedle application device and a microneedle array patch, where the microneedle application device is positioned against the target skin surface.

FIG. 2 is a cross sectional view of the microneedle application device 30 and a microneedle array patch 52, where the device 30 is positioned against the skin surface 32. The device 30 includes a support member or actuator. In the embodiment shown in FIG. 2, the support member or actuator is a piston 44 having a pad 46 and a shaft 48. In alternative embodiments, any type of mechanical, electromechanical, pneumatic, or other type of support member or actuator can be used.

A driver 50 capable of storing energy engages the shaft 48 of the piston 44, and can accelerate the piston 44 to a desired velocity. For example, the driver 50 may be in the form of a mechanical spring (e.g., a coil spring, leaf spring, etc.), compressed resilient member (e.g., rubber, etc.), compressed fluids (e.g., air, liquids, etc.), piezoelectric structure, electromagnetic structure, etc. The collar 40 can hold a patch 52, carrying a microneedle array, prior to patch application.

In operation, the microneedle application device 30 is positioned with the collar 40 near a desired application site. The contact portion 42 of the collar 40 is placed in contact with the skin surface 32, and the contact portion 42 defines a target patch application site 54 on the skin surface 32. A user will typically apply some force to the microneedle application device 30 at the gripping portion 36 of the housing 34. At least a portion of that force is generally transmitted through the collar 40 to the skin 32, and that force is referred to as a "pushdown force".

A "dome" 56 is generally created at the target site 54, as the skin 32 responds to the pushdown force. This "dome" has parameters of height and firmness. Both of these parameters of the dome are dependent upon the force applied to the applicator during microneedle application device 30 positioning. It is believed that the depth of penetration of a microneedle array is related to the application site, i.e., soft and fatty areas of a body vs. firm muscular areas of a body. Skin characteristics vary across species, and it is believed that particular characteristics of skin will vary across individual test subjects and across selected application sites on individual test subjects. Such variations can affect characteristics of the dome 56. In addition, a "pushback force" is exerted by the skin 32 in response to the pushdown force. The pushback force is generally directed in a direction directly opposed to the direction of the pushdown force, although specific relationships can be complex and will vary depending on the particular application site.

In the embodiment shown in FIG. 2, a force sensor is coupled to the piston 44 at either end or anywhere along the length of piston 44, for example, at location 58A, 58B and/or 58C (jointly referred to as sensor 58). The sensor 58 is capable of sensing applied mechanical forces, such as pushback force at the piston 44. The sensor 58 can be a strain gauge, variable capacitance sensor, or variable resistance sensor. In one embodiment, the sensor 58 comprises a variable resistance member having a semi-conducting polymer disposed between conductive layers or grids, where the resistance of the variable resistance member varies according to applied force. The variable resistance member is further configured in a voltage divider, which converts the resistance of the member into a voltage signal output that can be measured to detect force applied to the sensor 58. An example of such a variable resistance member is disclosed in U.S. Pat. No. 5,209,967, which is hereby incorporated by reference in its entirety. Other examples of aspects of such a variable resistance member are disclosed in U.S. Pat. Nos. 5,904,978 and 5,573,626. Another variable resistance member is commercially available as an Interlink FSR™ force sensing device available from Interlink Electronics, Inc., Camarillo, Calif.

In the microneedle application device 30, the piston 44 is moveable between a stored position and an extended position. In the stored position, energy is stored in the driver 50, and an actuator 38 secures the piston 44 in its stored position. The actuator 38 allows an operator to trigger the release of energy stored in the driver 50 to accelerate the piston 44 through the collar 40 and toward the patch 52

The microneedle application device 30 can be used to deliver the microneedle array patch 52 to the skin surface 32, in order to pierce the stratum corneum at the target application site 54 on a patient's skin. For example, the patch application device may be used to deliver drugs (including any pharmacological agent or agents) through the skin in a variation on transdermal delivery, or to the skin for intradermal or topical treatment, such as vaccination. Alternatively, the microneedle array patch 52 may be used to pierce the stratum corneum before or after a pharmacological agent is applied to the skin surface in a separate step, thus being used as a pre- or post-treatment step.

Figure 3:
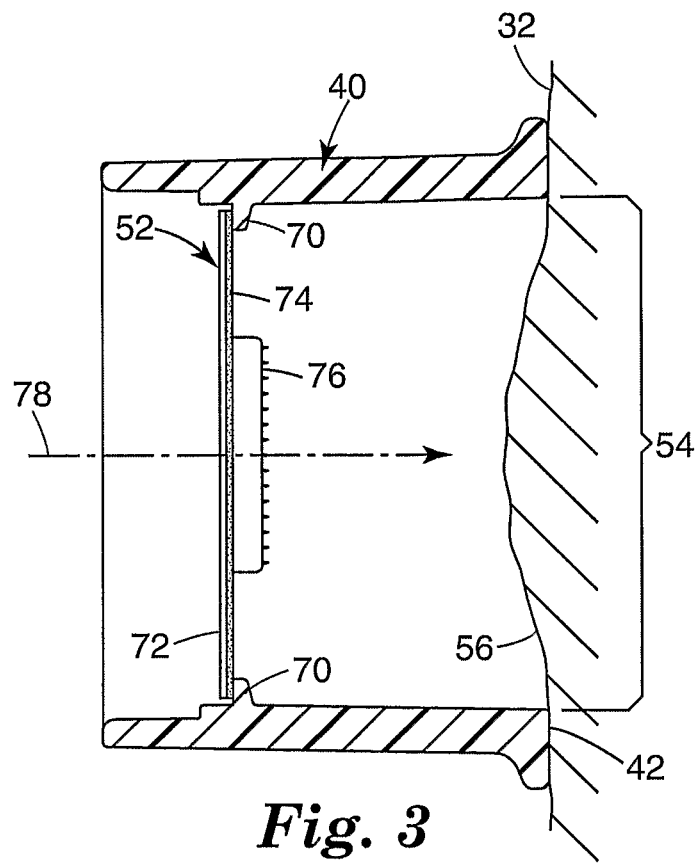
FIG. 3 is an enlarged cross sectional side view of a portion of the microneedle application device positioned against the target skin surface.

FIG. 3 is an enlarged cross sectional view of the collar 40 of the microneedle application device 30 positioned against the skin surface 32. The collar 40 includes obstructions 70 on an interior portion thereof. The obstructions 70 are configured to retain patches, such as the patch 52. Patch 52 includes a backing 72, an adhesive 74 (e.g., a pressure sensitive adhesive), and a microneedle array 76.

A desired patch application path 78 is defined through the collar 40. The path 78 is substantially perpendicular to a plane in which the microneedle array 76 is retained by the obstructions 70 within the collar 40, and is generally perpendicular to the target application site 54. It is desired that the patch 52 contact the target application site 54 with the patch 52 as close to parallel with the skin surface 32 as possible in order to promote proper microneedle array deployment and proper microneedle penetration of the stratum corneum.

In operation, the patch 52 is moved along the patch application path 78. This patch movement can be accomplished by mechanically pushing the patch 52 with the piston 44. In alternative embodiments, the microneedle application device 30 can use other means for moving the patch 52. For example, the patch 52 can be moved pneumatically, without contacting a piston.

Figure 4A:
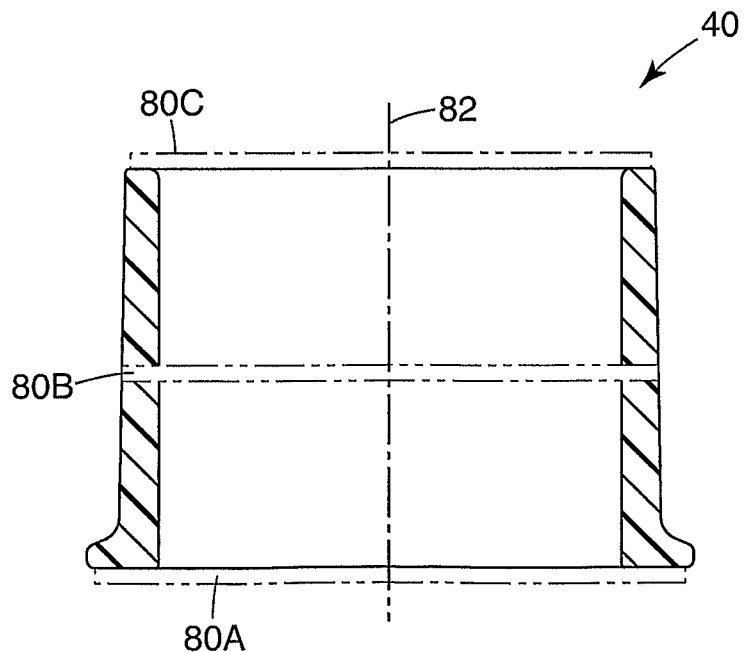
FIG. 4A is a cross sectional side view of a portion of the microneedle application device.

FIG. 4A is a cross sectional side view of the collar 40 of the microneedle application device 30. As shown in FIG. 4A, at least one sensor is coupled to a portion of the collar 40 at either end or anywhere along the length of the collar, for example, at location 80A, 80B and/or 80C (jointly referred to as sensor 80). An axis 82 is defined through the interior of the collar 40. In embodiments of the microneedle application device 30 using a piston to move the patch 52, the axis 82 is generally aligned with a central axis of the piston 44. A sensor arranged relative to any of locations 80A-80C will sense forces applied to the collar 40, such as pushback force. In embodiments where variable resistance sensors are utilized, the sensor can be positioned adjacent one or more actuator structures, such as set screws, feet, struts, etc., that are used to contact and compress the variable resistance member of the sensor 80.

Figure 4B:
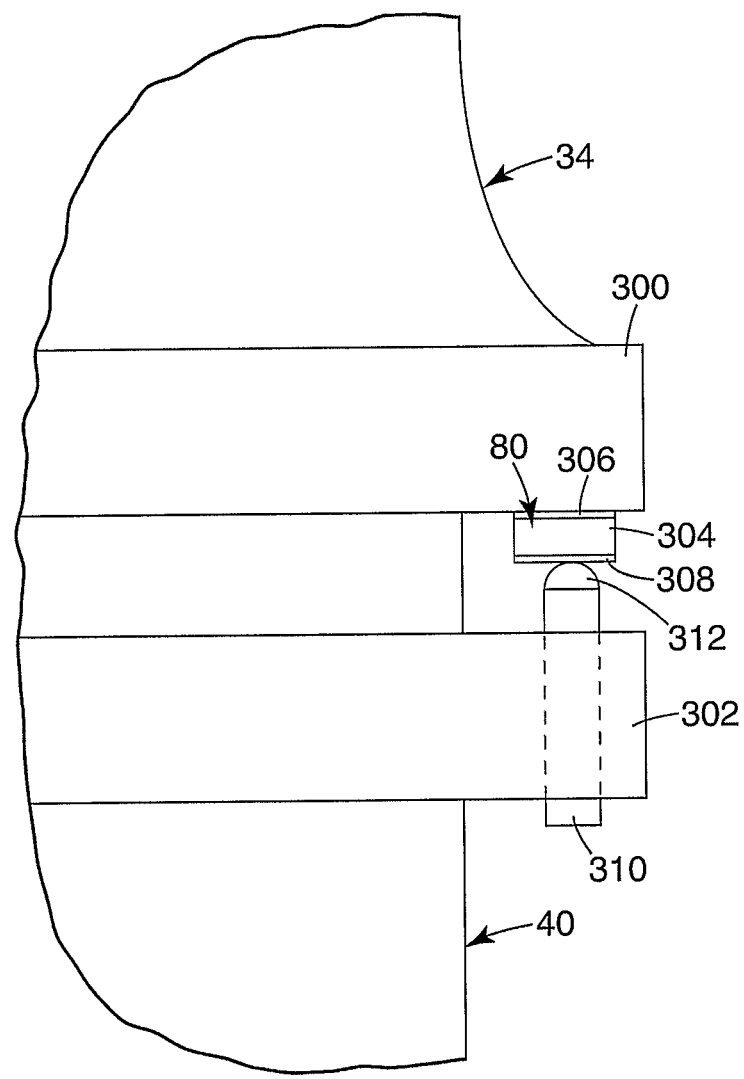
FIG. 4B is a schematic side view of a portion of an alternative embodiment of the microneedle application device.

FIG. 4B is a schematic side view of portions of a housing 34 and a collar 40 of an alternative embodiment of the microneedle application device. The housing 34 has an annular protrusion 300 and the collar 40 has an annular protrusion 302. The annular protrusions 300 and 302 are generally positioned adjacent each other in a spaced relationship. A sensor 80 for sensing force at the collar 40 is positioned on annular protrusion 300. The sensor 80 includes a variable resistance layer 304 disposed between a pair of conductive layers 306 and 308. A set screw 310 is disposed in annular protrusion 302 and has a generally hemispherical contact surface 312 located at one end of the set screw 310. The contact surface 312, which can be formed of a polymer material, is arranged to face the sensor 80. Adjustment of the set screw 310 allows the contact surface 312 to be positioned in contact with or spaced as much as desired to the sensor 80. Relative movement between the annular protrusions 300 and 302 allows force to be transmitted from the contact portion 312 to the sensor 80 located at a perimeter of the collar 40, which senses associated forces. It will be recognized that additional sensors can be incorporated along the annular protrusions 300 and 302.

Figure 5A:
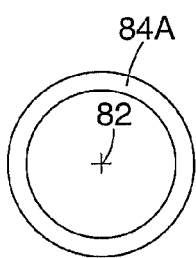
FIGS. 5A-5C are schematic representations of force sensitive regions at a target application site for alternative collar sensor arrangements.
Figure 5B:
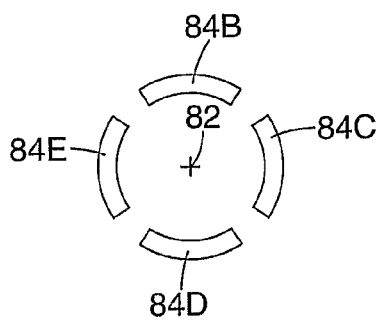
Figure 5C:
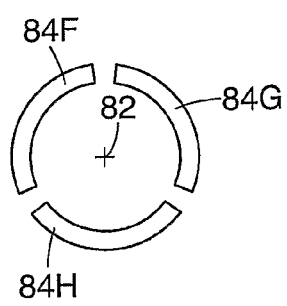

FIGS. 5A-5C are schematic representations of force sensitive regions for alternative sensor arrangements at the contact portion 42 of the collar 40. While FIGS. 5A-5C depict arrangements of sensors along the contact portion 42, corresponding to sensor location 80A in FIG. 4A, similar sensor arrangements are possible regardless of what axial location on the collar 40 the sensors are located. Moreover, further sensor arrangements are contemplated within the scope of the present invention, and can include any number of individual sensors and/or sensor regions.

FIG. 5A is a representation of a single sensor region 84A extending in a generally circular shape around the axis 82. FIG. 5B is a four-sensor configuration, with sensor regions 84B-84E arranged in a generally circular shape around the axis 82. The sensor regions 84B-84E are arranged in four generally equal segments that are substantially equally spaced apart, with each sensor region arranged at approximately 90 degree increments around the axis 82. FIG. 5C is a three-sensor configuration, with sensor regions 84F-84H arranged in three generally equal segments that are substantially equally spaced apart, with each sensor region arranged at approximately 120 degree increments around the axis 82. It will be understood that the sensor regions 84B-84H can correspond to discrete sensor elements or to discretely sensitive regions of one or more sensors. That is, a single sensor may have one or more force sensing elements or discretely sensitive regions. In one embodiment, (not shown) the force sensitive regions 84F-84H may be small circular sensors that are partially recessed in and evenly spaced around the contact portion 42 of the collar 40. Embodiments of a microneedle application device 30 with one or more sensors positioned on the collar 40 permit detection of an orientation of the device 30 relative to the skin surface 32. This, in turn, permits feedback generation as to the orientation of the patch 52 relative to the target application site 54, which can be used to predict and characterize the patch application path 78. For example, looking to the sensor arrangement shown in FIG. 5B, larger forces sensed at sensor regions 84B and 84C than at sensor regions 84D and 84E correspond to unequal force distribution at the collar 40. Such unequal force distribution can indicate that force applied to the microneedle application device 30 by an operator is skewed, and could lead to undesirable and improper patch application.

Figure 6:
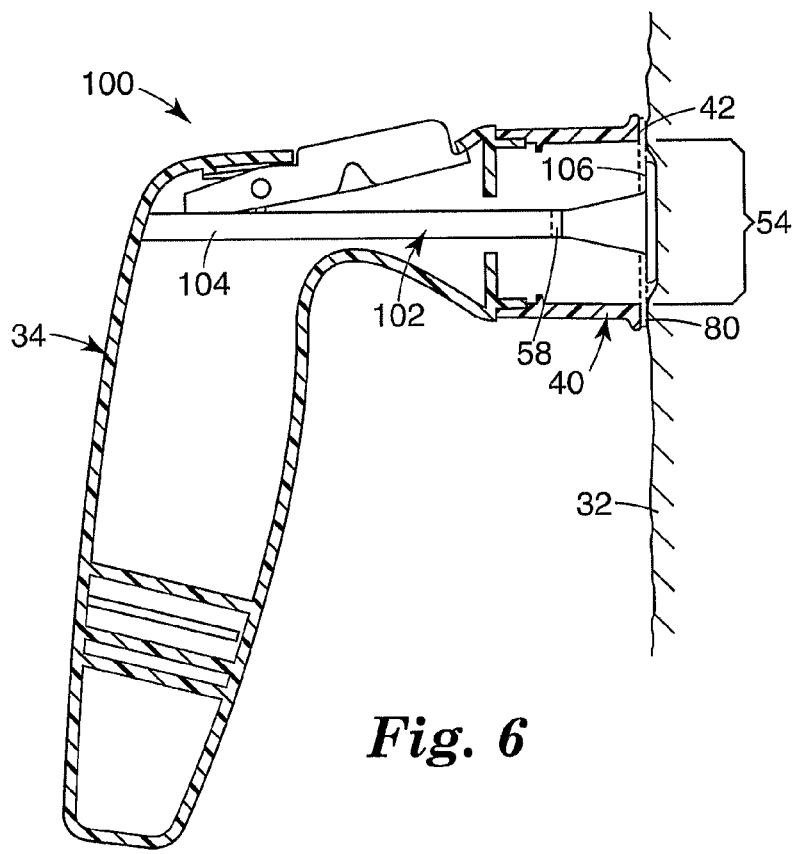
FIG. 6 is a cross sectional side view of a diagnostic tool.

While feedback provided according to the present invention is useful at the time of microneedle application, such feedback is also useful in broader contexts, including training and research settings that may precede or follow patch application. For instance, feedback sensing can be accomplished with purely diagnostic tools. FIG. 6 is a cross sectional view of a diagnostic tool 100. In the embodiment shown in FIG. 6, the housing 34 and many other components of the diagnostic tool 100 are shaped to simulate a microneedle application device, such as the microneedle application device 30 of FIGS. 1 and 2. Similarities permit the diagnostic tool 100 to be used in training and research procedures applicable to use of microneedle application devices.

As shown in FIG. 6, the diagnostic tool 100 includes a support structure 102 having a shaft 104 fixed within the housing 34 and a pad 106 that extends up to or beyond the contact portion 42 of the collar 40. The support structure 102 is generally shaped to simulate a microneedle application piston in an extended position. In alternative embodiments, the diagnostic tool 100 includes a movable piston.

The diagnostic tool 100 further includes a sensor 58 positioned at an interior portion along the support structure 102 and at least one sensor 80 positioned at the contact portion 42 of the collar 40. Sensor locations shown in FIG. 6 are exemplary, and other sensor arrangements are possible. Moreover, either sensor 58 or 80 could be omitted, and additional sensors at other locations (e.g., on portions of the housing 34) could be included.

Figure 7A:
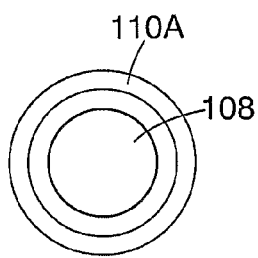
FIGS. 7A-7C are schematic representations of force sensitive regions at a target site for alternative sensor arrangements.
Figure 7B:
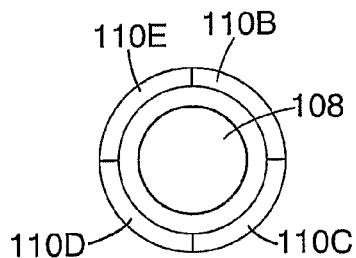
Figure 7C:
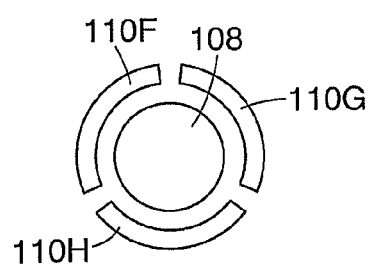

FIGS. 7A-7C are schematic representations of force sensitive regions at a target site for alternative sensor arrangements. FIG. 7A shows a pad sensor region 108, corresponding to sensor 58 on support structure 102 in FIG. 6, and a single collar sensor region 110A generally surrounding the pad sensor region 108. FIG. 7B shows the pad sensor region 108 and four collar sensor regions 110B-110E generally surrounding the pad sensor region 108. The collar sensor regions 110B-110E are arranged in four generally equal segments that are substantially equally spaced apart, with each sensor region arranged at approximately 90 degree increments around the pad sensor region 108. FIG. 7C shows the pad sensor region 108 and three collar sensor regions 110F-110H generally surrounding the pad sensor region 108. The collar sensor regions 110F-110H are arranged in three generally equal segments that are substantially equally spaced apart, with each sensor region arranged at approximately 120 degree increments around the pad sensor region 108. While the sensor arrangements in FIGS. 7A-7C have been described with respect to the diagnostic tool 100 of FIG. 6, the sensor arrangements can be equally applied with a microneedle application device, such as that shown and described with respect to FIGS. 1 and 2.

Although various embodiments are illustrated in the FIGS. 1-7, it should be appreciated that any suitable microneedle application device may be configured with force sensors as described above. For example, suitable microneedle application devices include those described in U.S. Patent Application Publications Nos. US 2002/0091357 A1, US 2002/0123675 A1, and US 2002/0087182; International Patent Application Nos. PCT/US2005/041870 and PCT/US2005/041854, both filed on Nov. 18, 2005, and U.S. Patent Application Ser. No. 60/694,447 filed on Jun. 27, 2005.

Figure 8A:
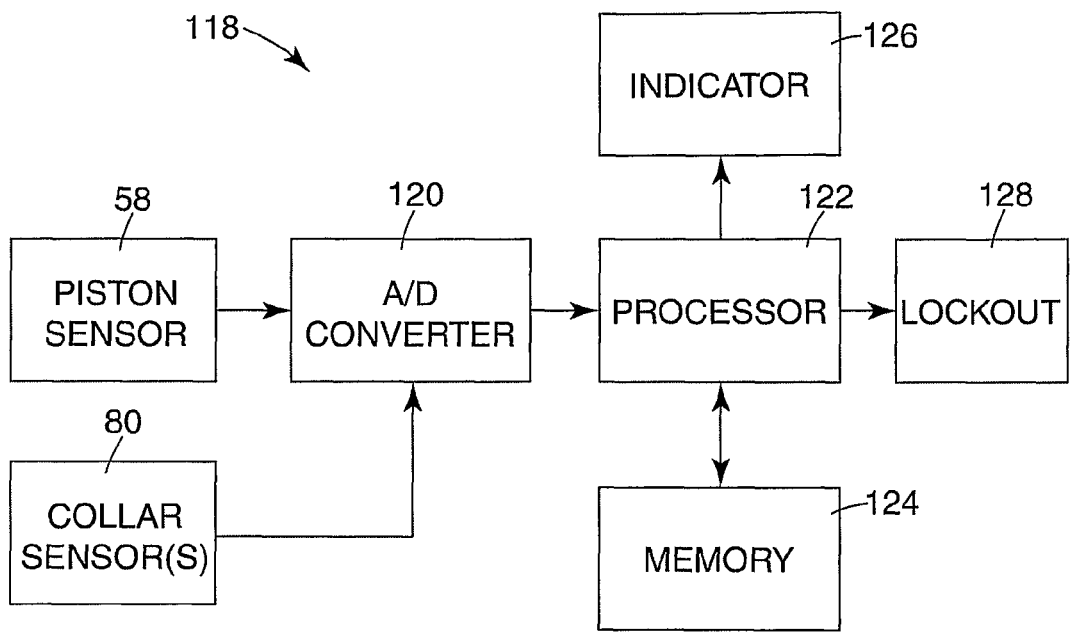
FIG. 8A is a block diagram of a digital feedback system.

FIG. 8A is a block diagram of a digital feedback system 118. FIG. 8A is simplified for clarity. It will be recognized that other components and circuitry can be included, as needed and desired. Digital feedback system 118 senses forces using piston sensor 58 and one or more collar sensors 80. Signals from the sensors 58 and 80 are supplied through appropriate circuitry to an analog/digital (A/D) converter 120. The A/D converter 120 is operably connected to a processor 122. The processor 122 can communicate with memory 124, which can include a database for storing sensed data, and an indicator 126. The processor can be located in a computer that is operably connected to sensors 58 and 80. The processor 122 can adjust and manipulate raw data sensed by the sensors 58 and 80 as desired for output display or storage in a database. The indicator 126 can, for instance, inform an operator regarding the relative orientation of the device or tool, and the indication provided can incorporate data from multiple sensors. The indicator 126 can provide an indication in numerous forms, be they visual, audible, tactile, etc.

In addition, the system 118 can include a lockout mechanism, such as lockout 128. The lockout 128 can prevent an operator from applying a patch unless magnitude of a sensed applied force is within a preferred range. Such a preferred range can consist of a single force value for sensor configurations such as that shown and described with respect to FIG. 5A or with respect to multiple force values obtained from multiple sensor arrangements such as those shown and described with respect to FIGS. 5B, 5C, 7A, 7B and 7C. Alternatively or in addition, the lockout 128 can permit patch application only when the device or tool is in a particular desired position. In one embodiment, the lockout 128 can prevent patch application by preventing the trigger 38 (shown in FIGS. 1 and 2) from being actuated. In an alternative embodiment, the sensor(s) can provide direct feedback to the trigger 38, thereby activating the trigger only when the tool has been placed into a particular desired position.

It will be recognized that components of the system 118 can be wholly contained on or within a tool, or one or more components can be located externally. Components of the system 118 can be connected by a physical or wireless (e.g., radio wave) connection, and can include transmission of data and signals over a network or the Internet.

Figure 8B:
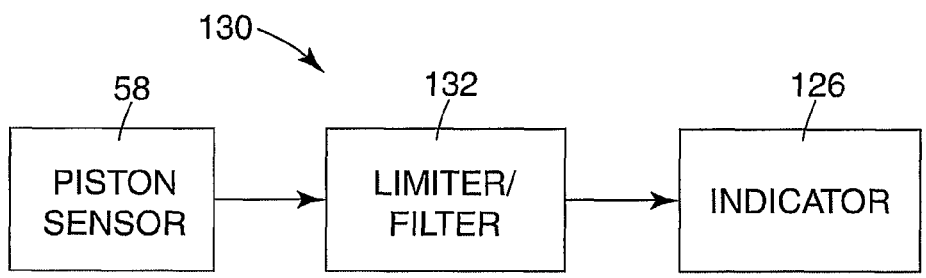
FIG. 8B is a block diagram of an analog feedback system.

FIG. 8B is a block diagram of an analog feedback system 130, which includes a piston sensor 58 electrically connected to a limiter/filter 132, and an indicator 126. The limiter/filter 132 can provide bandwidth limiting (e.g., with low and/or high pass filters), linearization of sensed force responses, and gain adjustment. The analog feedback system 130 can include other components and circuitry, not shown in FIG. 8B for clarity, as needed and desired. In further embodiments, one or more additional sensors (e.g., collar sensors 80 as shown in FIG. 8A) can also be electrically connected to the limiter/filter 132. Additionally, it will be recognized that components of the system 130 can be wholly contained on or within a tool, or one or more components can be located externally. Moreover, in alternative embodiments, any combination of analog and digital circuitry can be implemented as desired.

Figure 9A:
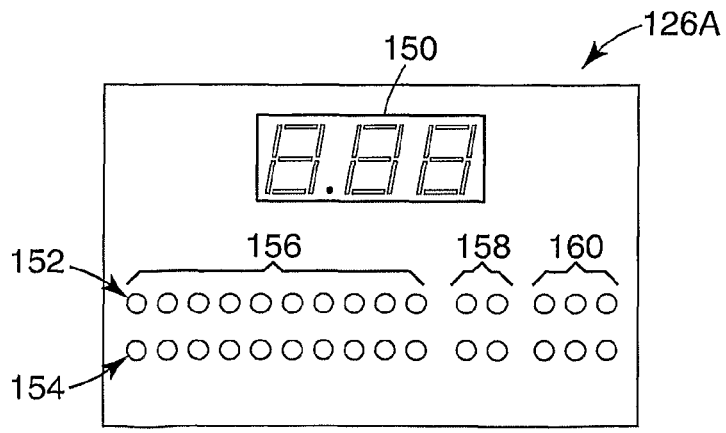
FIGS. 9A-9C illustrate alternative indicators for displaying sensed force and/or tool orientation data according to the present invention.
Figure 9B:
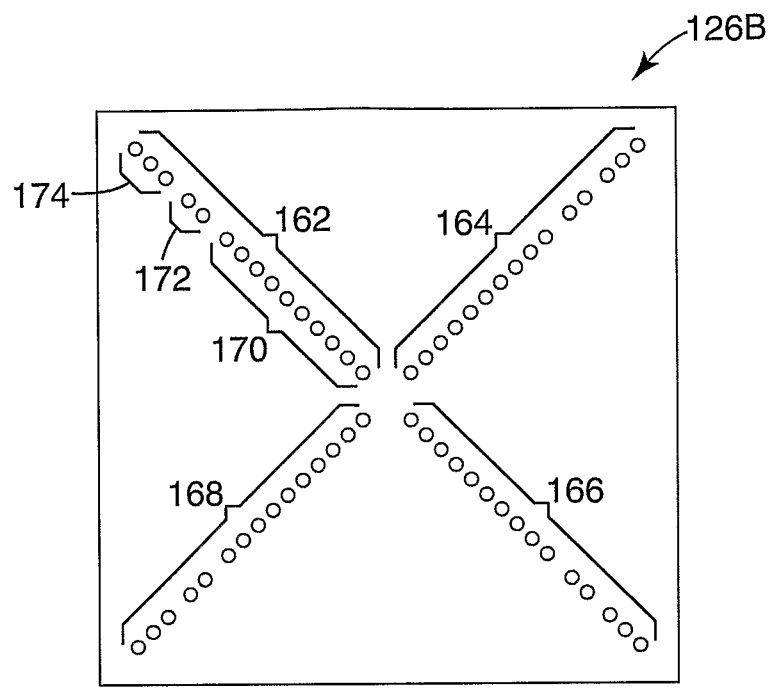
Figure 9C:
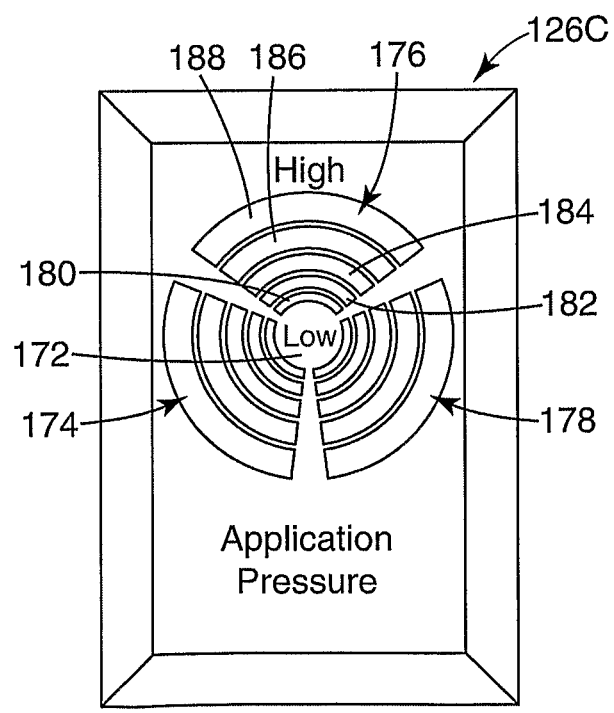

FIGS. 9A-9C illustrate exemplary indicators for displaying sensed force and/or tool orientation data according to the present invention. FIG. 9A shows an indicator 126A having a readout display 150 for showing quantitative force output sensed, and a pair of visual meters 152 and 154. The indicator 126A could indicate an output derived from any sensor on a tool, such as sensors 58 and 80 shown and described above. In the embodiment shown in FIG. 9A, the readout display 150 is a digital display, such as a 3½ digit liquid crystal display (LCD). In further embodiments, the readout display 150 can be any type of digital or analog display, such as a dial. In the embodiment shown in FIG. 9A, the pair of visual meters 152 and 154 are two rows of light emitting diodes (LEDs), with each row having three color regions 156, 158 and 160. For example, the color regions 156, 158 and 160 can correspond to green, yellow and red LEDs, respectively. One meter, for example meter 152, can provide a dynamic indication of force sensed at a collar of a tool (see, e.g., FIG. 5A), with more LEDs lighting from left to right to indicate greater force sensed. Meter 152 can also hold a maximum value for a desire period and then decay. The other meter (i.e., meter 154) can indicate average force applied. The readout display 150 and the visual meters 152 and 154 can be used on a real-time basis to assess the positioning of a tool relative to a target surface (e.g., the pushdown force applied by an operator), as well as to assess the suitability of a selected target site for microneedle application.

In an alternative embodiment, the indicator 126A can provide an indication of force sensed at multiple locations. For instance, meter 152 can indicate force sensed at a collar of a tool (see, e.g., sensor region 108 of FIG. 7A) and meter 154 can indicate force sensed at a support member or actuator of a tool (see, e.g., sensor region 110A of FIG. 7A). In such embodiments, the visual meters can have other shapes and arrangements (e.g., starburst shape, etc.) as desired for the particular context. Moreover, additional readout displays can be included with the indicator 126A. Each readout display can correspond to data for a particular sensor, or can correspond to processed data (e.g., averages, multiple sensor data trend data, etc.).

FIG. 9B shows an indicator 126B having four visual meters 162, 164, 166, and 168 generally arranged in an "X" shape. Each visual meter 162-68 can be color coded into multiple regions, with each region having nearly any color. Visual meter 162 is shown with a green region 170, a yellow region 172 and a red region 174, and the other visual meters 164, 166 and 168 can be color coded in the same manner. The visual meters 164, 166 and 168 can operate much in the same manner as described with respect to indicator 126A above. The X-shaped arrangement of the visual meters 162, 164, 166 and 168 can indicate force sensed from multiple sensors, for instance, each visual meter 162, 164, 166 and 168 can correspond to a sensing region 84B-84E as shown in FIG. 5B. Other arrangements of the visual meters 162, 164, 166 and 168 are contemplated, and will vary according to preference and factors such as the number and arrangement of sensors on the corresponding tool. Indicator 126B can be used to indicate the orientation of a tool relative to a surface, by indicating whether forces are evenly distributed about a portion of the tool (e.g., about the collar of a microneedle application device or, more specifically, about an annular collar of such a device). When provided on a real-time basis, such an indication can be used, by an operator, to adjust the orientation of the tool. In addition, as with indicator 126A described above, the indicator 126B can be used to adjust the magnitude of force applied to the tool by the operator.

FIG. 9C shows an indicator 126C having a binary display 172 and three visual meters 174, 176 and 178 located around the binary display 172. The arrangement of the visual meters 174, 176 and 178 can indicate force sensed from multiple sensors, for instance, each visual meter 174, 176 and 178 can correspond to sensor arrangements shown in FIGS. 5C and 7C. Each visual meter 174, 176 and 178 can have color coded regions 180, 182, 184, 186 and 188 that are, from the innermost region to the outermost region, red (180), yellow (182), green (184), yellow (186), and red (188). The green region 184 can indicate that force sensed is in a desirable range for microneedle application. The inner regions 180 (red) and 182 (yellow) can indicate insufficient force, and the outer regions 186 (yellow) and 188 (red) can indicate excessive force. The binary display 172 can indicate whether the force and/or orientation of a tool is proper or improper for microneedle application, and the ultimate binary output can accompany an analysis of a number of different force and orientation factors.

Other indicators can be used according to the present invention. For example, indicators can provide auditory output, such as from a sound generator (buzz, squeal, click, etc.) or enunciator (e.g., a voice output). The indicator can also provide an indication of force by varying the intensity of an output (e.g., light or sound intensity).

The indicator can be directly connected to the tool, or can be remotely located. For instance, with the system 118 shown and described with respect to FIG. 8A, the indicator can be a display on a computer. Where a computer is used, outputs can be processed for display by software, such as commercially available software packages like EXCEL spreadsheet software from Microsoft Corp., Redmond, Wash., MATLAB software from The MathWorks, Inc., Natick, Mass., and data acquisition and analysis software (e.g., LabVIEW) from National Instruments Corporation, Austin, Tex.

The ranges and limits of indicators can be set according to a value meaningful for the particular application, for instance, at a value that ensures a high degree of confidence for drug delivery by microneedle arrays. Specific values will vary depending on factors such as application device configuration, microneedle array configuration, molecules to be delivered, etc.

Figure 10A:
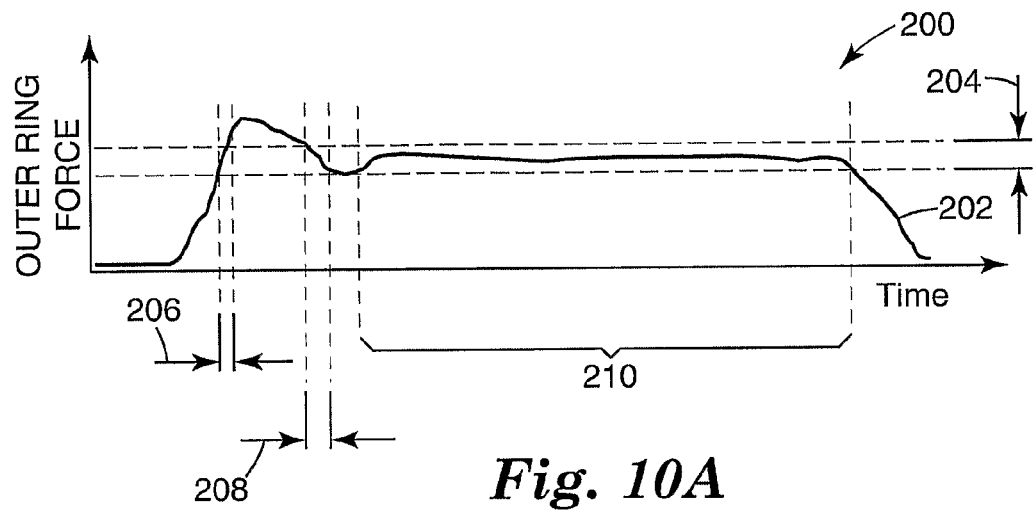
FIG. 10A is a graph of force sensed at a single sensor coupled to a collar of a tool versus time as the collar is positioned and adjusted against a skin surface, and a range of forces acceptable for microneedle application.
Figure 10B:
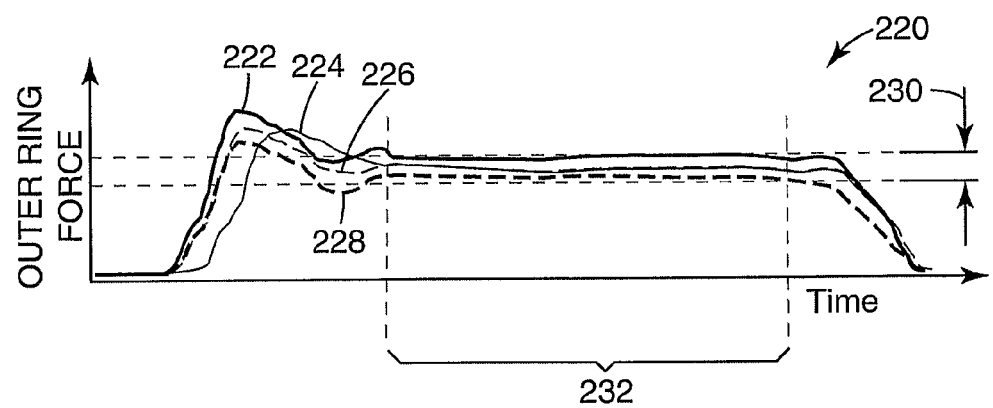
FIG. 10B is a graph of force sensed at four sensors coupled to a collar of a tool versus time as the collar is positioned and adjusted against a skin surface, and a range of forces acceptable for microneedle application.

The present invention allows analysis of sensed force data. FIG. 10A is a graph 200 with a curve 202 of force sensed at a single sensor located at a collar of a tool (see, e.g., FIG. 5A) versus time as the collar is positioned against a skin surface (see, e.g., FIG. 2), and a range 204 of forces acceptable for microneedle application. As shown in FIG. 10A, as the collar is positioned and adjusted against the skin surface, sensed force increases initially, then produces a dynamic response as an operator adjusts applied force while observing feedback indication(s), and then drop as the collar is moved away from the skin surface. Regions 206, 208 and 210 represent time periods when the curve 202 falls within the range 204, and correspond to one or more proper conditions for microneedle application. FIG. 10B is a graph 220 with four curves 222, 224, 226 and 228 representing force sensed at four sensors located at a collar of a tool (see, e.g., FIG. 5B) versus time as the collar is positioned and adjusted against a skin surface (see, e.g., FIG. 2), and a range 230 of forces acceptable for microneedle application. As shown in FIG. 10B, as the collar is positioned against the skin surface, sensed force increases initially, then produces a dynamic response as an operator adjusts applied force while observing feedback indication(s), and then drops as the collar is moved away from the skin surface. A region 232 represents a time period when all of the curves 222, 224, 226 and 228 fall within the range 230, and corresponds to one or more proper conditions for microneedle application.

Figure 11A:
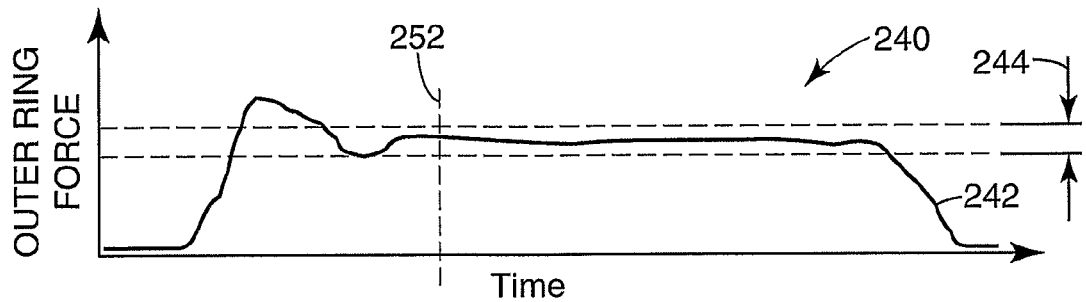
FIG. 11A is a graph of force sensed at a single sensor at a collar versus time as the collar is positioned and adjusted against a skin surface, and where no piston is actuated.

FIG. 11A is a graph 240 with a curve 242 representing force sensed at a single sensor located at a collar of a tool (see, e.g., sensor region 110A in FIG. 7A) versus time as the collar is positioned and adjusted against a skin surface (see, e.g., FIG. 2), and where no piston is actuated. A range 204 of forces acceptable for microneedle application is shown.

Figure 11B:
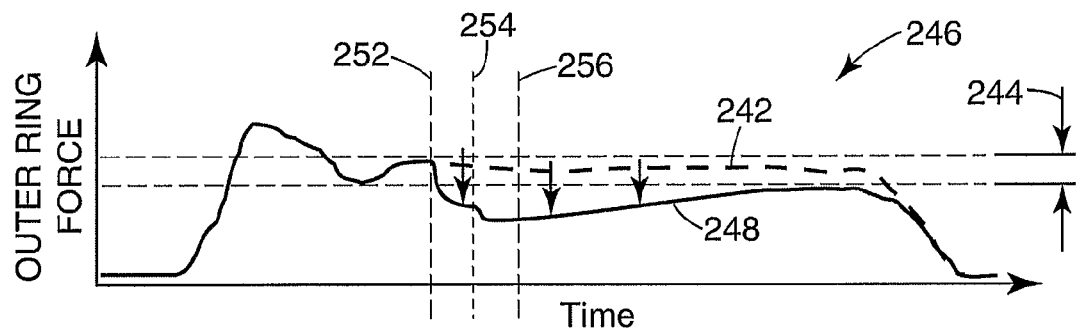
FIG. 11B is a graph of force sensed at a collar versus time as the collar is positioned and adjusted against a skin surface, and where a piston is actuated to eventually reach the skin surface.

FIG. 11B is a graph 246 with a curve 248 representing force sensed at a collar (see, e.g., sensor region 110A in FIG. 7A) versus time as the collar is positioned and adjusted against a skin surface. Patch application is triggered at time 250, while the curve 248 falls in the range 244, and then a pad of a piston of the applicator reaches the skin surface at time 252. At time 254, the collar and the piston are sharing forces between the applicator device and the skin surface. Then at time 256, the forces between the applicator device and the skin surface are approaching equilibrium. As shown in FIG. 11B, assuming the operator is holding the applicator steady and the target site does not move relative to the applicator, the force at the collar on curve 248 drops after the pad reaches the skin surface at time 252 (curve 242 is shown in phantom in FIG. 11B for comparative purposes).

Figure 11C:
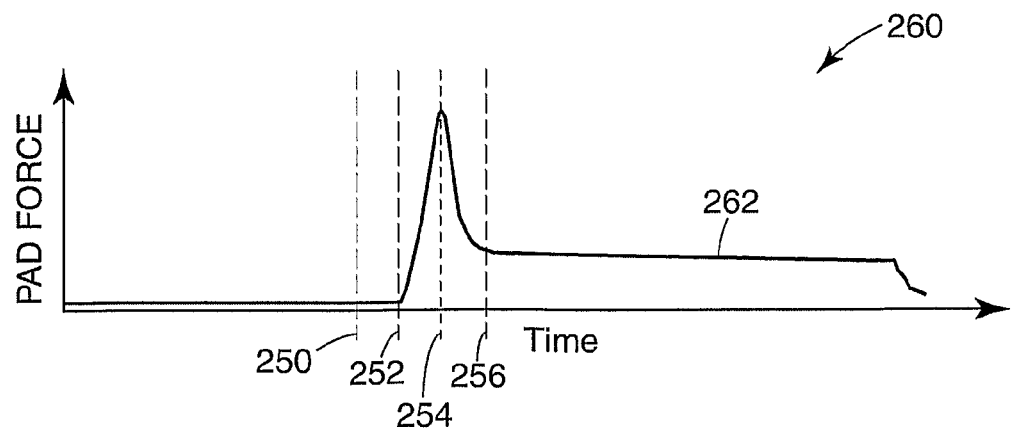
FIG. 11C is a graph of force sensed at a pad of the piston versus time as the collar is positioned against the skin surface, and where the piston is actuated to eventually reach the skin surface as in FIG. 11B.

FIG. 11C is a graph 260 with a curve 262 representing force sensed at the pad of the piston (see, e.g., sensor region 108 in FIG. 7A) versus time during the operation shown in FIG. 11B. As shown in FIG. 11C, the curve 262 increases from time 252 to time 254 after the pad initially reaches the skin surface, and then decreases from time 254 to time 256 as forces are shared between the piston and the collar.

Figure 12A:
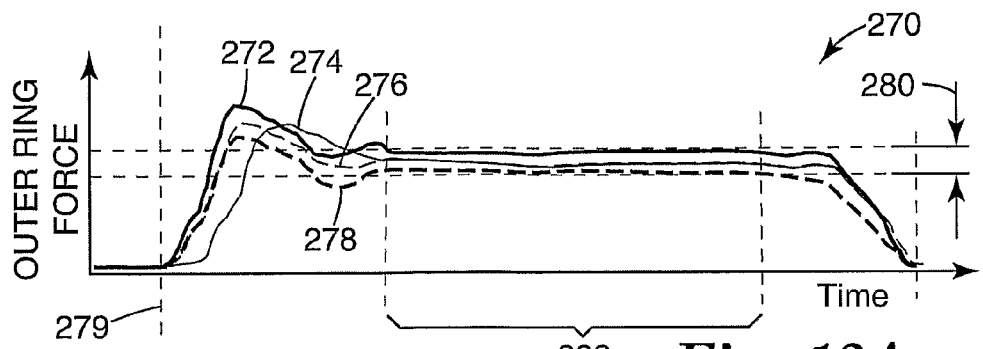
FIG. 12A is a graph of force sensed by four sensors coupled to a collar versus time, when the collar is positioned and adjusted against a skin surface, and where no piston is actuated.

FIG. 12A is a graph 270 with four curves 272, 274, 276 and 278 representing force sensed by four sensors located at a collar (see, e.g., sensor regions 110B, 110C, 110D and 110E in FIG. 7B) versus time as the collar is positioned and adjusted against a skin surface beginning at time 279, and where no piston is actuated. A range 280 of forces acceptable for microneedle application is shown. A region 282 represents a time period when all of the curves 272, 274, 276 and 278 fall within the range 280, and corresponds to one or more proper conditions for microneedle application.

Figure 12B:
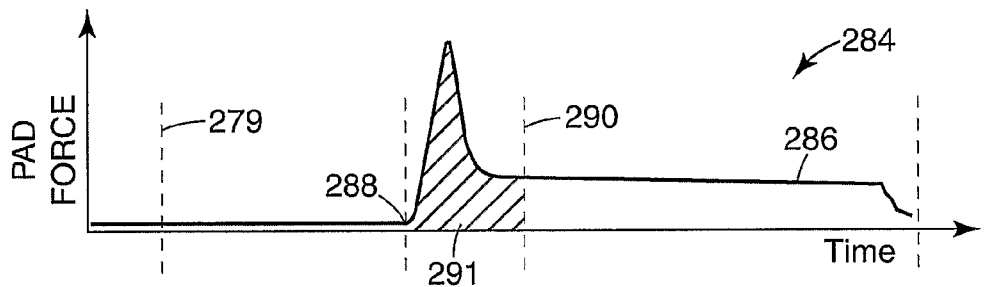
FIG. 12B is a graph of force sensed at a pad of a piston versus time when the collar is positioned against the skin surface, and where the piston is actuated to eventually reach the skin surface.

FIG. 12B is a graph 284 with a curve 286 representing force sensed at a pad of a piston (see, e.g., sensor region 108 in FIG. 7B) versus time when the collar is positioned and adjusted against the skin surface. Patch application is triggered and the pad of the piston reaches the skin surface at time 288. Force sensed at the pad approaches equilibrium at time 290. An area 291 is created under curve 286 between times 288 and 290.

Figure 12C:
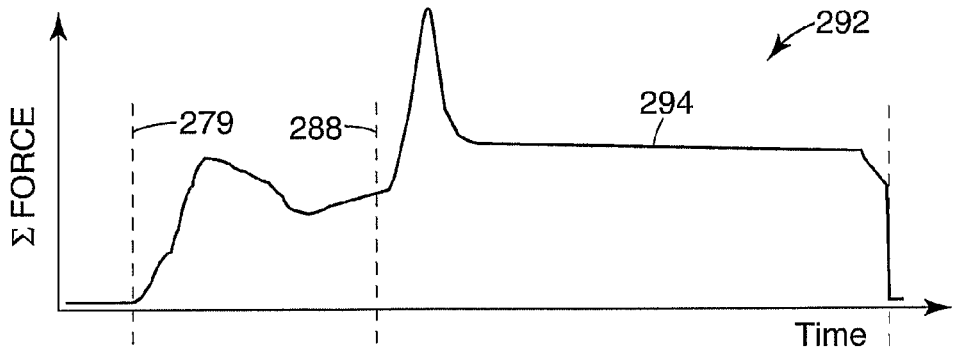
FIG. 12C is a graph of a sum of forces at the collar and the pad of the piston, as depicted in FIGS. 12A and 12B, versus time.

FIG. 12C is a graph 292 with a curve 294 representing a sum (Σ) of an average force at the collar (e.g., the sum of curves 272, 274, 276 and 278 divided by four) and the force at the pad of the piston (curve 286), as depicted in FIGS. 12A and 12B, versus time.

Figure 12D:
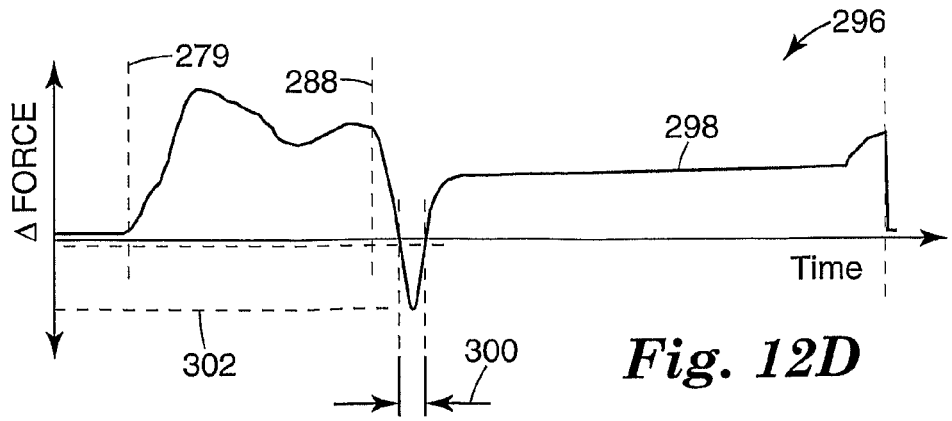
FIG. 12D is a graph of the force at the collar, as depicted in FIG. 12A, minus the force at the pad of the piston, as depicted in FIG. 12B, versus time.

FIG. 12D is a graph 296 with a curve 298 representing a force difference (Δ) between the average force at the collar (e.g., the sum of curves 272, 274, 276 and 278 divided by four), minus the force at the pad of the piston, as depicted by curve 286 in FIG. 12B, versus time. During a time interval 300, the values of curve 298 are negative, and reach a peak negative value 302. It is possible to correlate a time interval (e.g., the time interval 300) where the force difference Δ of graph 296 is negative with a particular assessment of patch application. For instance, a particular time interval where the force differential is negative may be correlated with a "good", desirable or proper patch application procedure and an appropriate output produced for recordation or indication to an operator. Further analysis of sensed data can be based upon magnitude, time (duration), area above or below curves, and other criteria.

The particular ranges 204, 230, 244, 280 of acceptable forces for microneedle application may vary and might depend on a number of factors including, but not limited to, the size, number, and shape of the microneedles, the type and amount, if any, of pharmacological agent being applied, the type and location of the skin surface, and the desired therapeutic response.

The present invention permits more consistent microneedle array application by providing feedback as to application parameters. For instance, where sensors are provided on both a collar and a piston of a microneedle application device, pushback force can be sensed and measured in relation to skin doming at a specific target site. In addition, for example, the recoil effect, if any, during patch application can be sensed and assessed.

Sensed data can assist in real-time site selection and patch application procedures. Real-time feedback allows an operator to obtain reliable characterizations of application procedure parameters without relying on muscle memory or other training-dependent factors for consistent and reliable patch application. Sensed data can also be used, in some situation, to adjust forces applied to move a patch toward a target application site, such as by selecting an appropriate applicator or in conjunction with adjusting a variable force driver.

Thus, the present invention provides the ability to measure and diagnose parameters associated with a particular target site for microneedle application as they directly apply to the chosen application device (or tool). This is advantageous over other devices as it allows for characterization of an application site by determining the specific site variable of skin pushback force relative to applied force. The present invention can also be used to assess the angle of application, i.e., the orientation of the tool, to assist the user in positioning the tool perpendicular to the target site by assuring that generally even pressure is applied over three or more force sensor regions at a contact portion of the tool.

In addition, the present invention has advantages for use in pre-clinical testing on non-human animals in order to better correlate research data to human testing and other subsequent application contexts. For all the foregoing reasons, the present invention has advantages over current technology in its ability to assess a site specifically for microneedle application. The specified advantages, however, should not be considered limiting in any way to the overall scope or utility of the invention.

Although the present invention has been described with reference to several alternative embodiments, workers skilled in the art will recognize that changes may be made in form and detail without departing from the spirit and scope of the invention. For instance, tools contemplated for use with the system and method of feedback sensing of the present invention can include a variety of applicators, such as applicators of any type of patch. In addition, all the graphs of FIGS. 10A-12D are merely exemplary, and graphs having other shapes and characteristics, and describing different parameters can be obtained according to the present invention.

The invention claimed is:

1. A microneedle application device for moving a microneedle array toward a target skin location, the microneedle application device comprising:
 a portion of the microneedle application device adapted for skin contact at least prior to microneedle application; and
 a feedback sensor operably connected to the microneedle application device, wherein the feedback sensor is capable of generating an output corresponding to forces between the target skin location and the portion of the microneedle application device at least prior to microneedle application;
wherein the microneedle array comprises two or more microneedles each comprising a height of no greater than about 250 micrometers; and wherein the feedback sensor comprises one or more sensor regions positioned to sense the force between the portion of the microneedle application device adapted for skin contact and the target skin location and
further comprising an additional sensor region operably connected to a piston of the microneedle application device.

2. The microneedle application device of claim 1, further comprising an indicator operably connected to the sensor regions, wherein the indicator is capable of indicating when the microneedle application device is in a desired orientation relative to the target application site for microneedle application.

3. The microneedle application device of claim 1 further comprising at least two additional sensor regions, each force sensing element being operably connected to the portion of the microneedle application device adapted for skin contact at least prior to microneedle application.

4. The microneedle application device of claim 3, wherein at least one of the sensor regions is located at or near a perimeter of the portion of the microneedle application device adapted for skin contact at least prior to microneedle application.

5. The microneedle application device of claim 3, wherein the sensor regions are positioned about an axis and are substantially equally spaced apart along a circumference defined around the axis.

6. The microneedle application device of claim 4, wherein the sensor regions each provide an output indicating desirability of an orientation of the microneedle application device relative to the target application site.

7. The microneedle application device of claim 1, wherein the sensor regions provide a quantitative output indicating force sensed.

8. The microneedle application device of claim 1, further comprising a processor operatively connected to the sensor regions for processing data from the force sensing element.

9. The microneedle application device of claim 1, further comprising a lockout for preventing application of the microneedle array under conditions determined as a function of the output generated by the feedback sensor.

10. The microneedle application device of claim 1, wherein each microneedle of the microneedle array comprises a height of at least about 100 micrometers.

11. A method of microneedle application, the method comprising:
 providing a microneedle applicator device of claim 1
 providing a microneedle array, wherein the microneedle array is mountable relative to the microneedle applicator device;
 positioning a locating portion of the microneedle applicator device in contact with skin at least prior to microneedle application to substantially define a target application site on the skin for application of the microneedle array;
 sensing a force between the target application site and a first portion of the microneedle applicator device;
 positioning the microneedle applicator device such that the microneedle array can be moved into contact with the skin along a path that is substantially orthogonal relative to the target application site; and
 moving the microneedle array toward the target application site.

12. The method of claim 11, wherein the first portion of the microneedle applicator device corresponds to a microneedle array deploying piston.

13. The method of claim 11, wherein the first portion of the microneedle applicator device corresponds to the locating portion.

14. The method of claim 13 and further comprising sensing a force between the target application site and a second portion of the microneedle applicator device.

15. The method of claim 14, wherein the second portion of the microneedle applicator device corresponds to a microneedle array deploying piston.

16. The method of claim 15 and further comprising correlating force sensed between the target application site and the first portion of the microneedle applicator device to force sensed between the target application site and the second portion of the microneedle applicator device.

17. The method of claim 11, further comprising providing an indication to an operator whether or not the microneedle applicator device is positioned for proper microneedle array application.

* * * * *